United States Patent
Kreuder et al.

(10) Patent No.: US 6,316,591 B1
(45) Date of Patent: Nov. 13, 2001

(54) ORDERED POLY(ARYLENE-VINYLENE) TERPOLYMERS, METHOD FOR THE PRODUCTION AND THE USE THEREOF AS ELECTROLUMINESCENT MATERIALS

(75) Inventors: Willi Kreuder, Mainz; Hans-Heinrich Hörhold, Jena; Henning Rost, Erlangen; Annett Hartmann, Jena, all of (DE)

(73) Assignee: Aventis Research & Technologies GmbH & Co. KG (DE)

( * ) Notice: Subject to any disclaimer, the term of this patent is extended or adjusted under 35 U.S.C. 154(b) by 0 days.

(21) Appl. No.: 09/308,057

(22) PCT Filed: Nov. 3, 1997

(86) PCT No.: PCT/EP97/06051

§ 371 Date: Aug. 13, 1999

§ 102(e) Date: Aug. 13, 1999

(87) PCT Pub. No.: WO98/21262

PCT Pub. Date: May 22, 1998

(30) Foreign Application Priority Data

Nov. 13, 1996 (DE) .............................. 196 46 877

(51) Int. Cl.$^7$ .................................. C08G 79/02
(52) U.S. Cl. .................. 528/398; 528/223; 528/242; 428/640; 428/524; 428/917
(58) Field of Search .................. 528/398, 223, 528/242; 428/690, 524, 917

(56) References Cited

FOREIGN PATENT DOCUMENTS

| 0637621 | 2/1995 | (EP) . |
| 0672741 | 9/1995 | (EP) . |

OTHER PUBLICATIONS

Chem Abstract: 125: 34410 "Nitrogeneous Polymers Used as Electroluminescent Materials" "Kreuder et al" 1996.*
125:99554 Poly (p–phenylene vinylene) Derivatives and Their Use As Electroluminescent Materials "Kreuder et al" 1996.*
124:345038 "Poly (p–phenylene vinylene) Derivatives and Their Use as Electroluminescent Materials" Kreuder et al 1996.*

* cited by examiner

Primary Examiner—Duc Truong
(74) Attorney, Agent, or Firm—Frommer Lawrence & Haug LLP

(57) ABSTRACT

Ordered poly(arylene-vinylene)terpolymers, process for their preparation and their use as electroluminescence materials Poly(arylene-vinylene) terpolymers comprising repeating units of the formula (I),

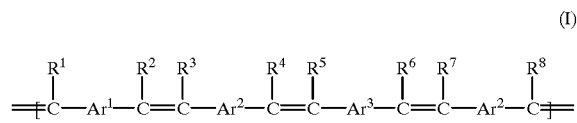

where the symbols have the following meanings:

$Ar^1, Ar^2, Ar^3$ are identical or different and are monocyclic or polycyclic, substituted or unsubstituted aryl or heteroaryl groups which may be linked via one or more bridges or be fused, $R^1, R^2, R^3, R^4, R^5, R^6, R^7, R^8$ are identical or different and are each H or a hydrocarbon radical having from 1 to 22 carbon atoms which may be substituted, preferably by F, and may also contain heteroatoms, preferably O, are suitable as electroluminescence materials.

11 Claims, No Drawings

ORDERED POLY(ARYLENE-VINYLENE) TERPOLYMERS, METHOD FOR THE PRODUCTION AND THE USE THEREOF AS ELECTROLUMINESCENT MATERIALS

There is a great industrial need for large-area solid-state light sources for a series of applications, predominantly in the field of display elements, VDU technology and lighting technology. The demands made of these light sources can at present not be met fully satisfactorily by any of the existing technologies.

As alternatives to conventional display and lighting elements, e.g. incandescent lamps, gas discharge lamps and non-self-illuminating liquid crystal display elements, use has been made for some time of electroluminescence (EL) materials and devices such as light-emitting diodes (LEDs).

WO 90/13148 and EP-A 0 443 861 describe electroluminescence devices comprising a film of a conjugated polymer as light-emitting layer (semiconductor layer). Such devices offer numerous advantages such as the opportunity to produce large-area, flexible displays simply and inexpensively. In contrast to liquid crystal displays, electroluminescence displays are self-illuminating and therefore require no additional backward illumination source.

According to WO 90/13148, poly(p-phenylene-vinylene) (PPV) is used as polymeric material for the light-emitting layer and it is proposed that the phenyl group in such a material be substituted or be replaced by other carbocyclic or heterocyclic aromatic ring systems.

Poly(p-phenylene-vinylene) derivatives for use as electroluminescence materials are also known from, for example, WO/A 96/10617 and PCT/EP 96/01066.

Although good results have been achieved with such materials, the property profile of these polymers is still capable of a great deal of improvement.

Since, in addition, the development of electroluminescence materials, particularly those based on polymers, can in no way be regarded as being concluded, the manufacturers of lighting and display devices are still interested in a wide variety of electroluminescence materials for such devices.

One reason for this is that only the interaction of the electroluminescence material with the other components of the devices allows conclusions to be drawn as to the suitability of the electroluminescence material.

It is therefore an object of the present invention to provide new electroluminescence materials which are suitable, when used in lighting or display devices, for improving the property profile of these devices.

It has now surprisingly been found that certain ordered poly(arylene-vinylene) terpolymers are particularly suitable as electroluminescence materials.

The invention accordingly provides a terpolymer comprising repeating units of the formula (I), (I)

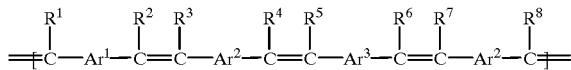

where the symbols have the following meanings:
$Ar^1$, $Ar^2$, $Ar^3$ are identical or different and are monocyclic or polycyclic, substituted or unsubstituted aryl or heteroaryl groups which may be linked via one or more, preferably one, bridge or be fused and preferably have from 2 to 100, particularly preferably from 2 to 50, very particularly preferably from 2 to 20, carbon atoms;

$R^1$, $R^2$, $R^3$, $R^4$, $R^5$, $R^6$, $R^7$ $R^8$ are identical or different and are each H or a hydrocarbon radical having from 1 to 22 carbon atoms which may be substituted, preferably by F, and may also contain heteroatoms, preferably O;
with the proviso that $=CR^1-Ar^1-CR^2=$, $=CR^3-Ar^2-CR^4=$ and $CR^5-Ar^3-CR^6=$ are each different from one another.

For the purposes of the invention, different means that they are at least regioisomers or stereoisomers or the radicals $Ar^1$, $Ar^2$, $Ar^3$ at least have different substitution patterns.

Terpolymers in the context of the invention are ternary copolymers.

The polymers of the invention generally have from 2 to 1000, preferably from 3 to 500, particularly preferably from 4 to 300, repeating units, preferably of the formula (I).

Preference is given to polymers consisting of repeating units of the formula (I).

Preference is also given to polymers comprising repeating units of the formula (I) in which $R^7$ and $R^8$ are, pairwise, identical to $R^3$ and $R^4$ respectively.

Preference is likewise given to polymers comprising repeating units of the formula (I) in which the symbols have the following meanings:
$Ar^1$, $Ar^2$, $Ar^3$ are identical or different and are

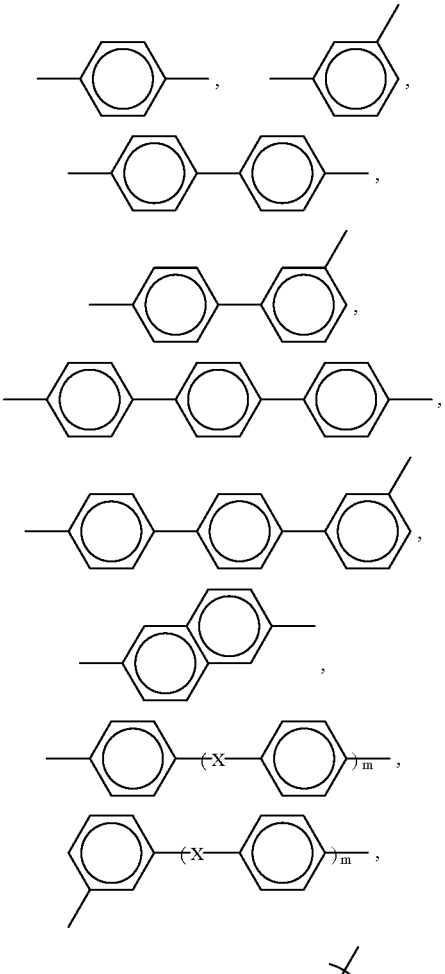

-continued

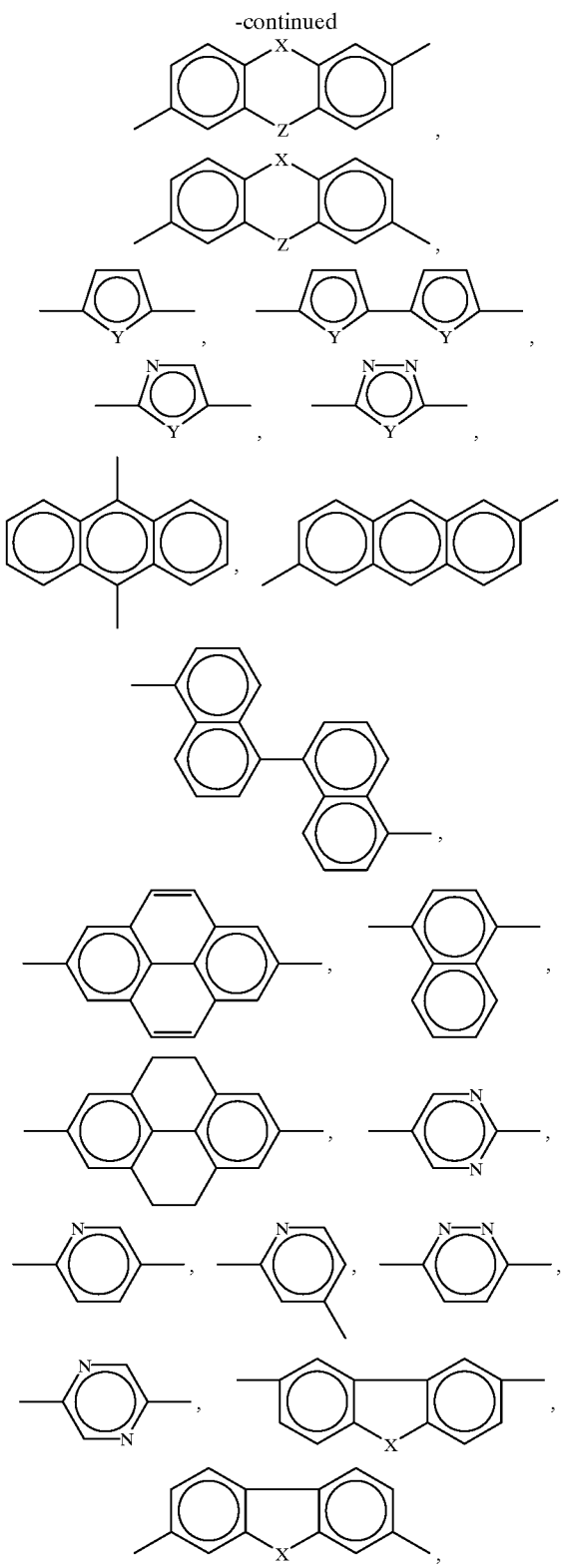

where
Ar$^1$, Ar$^2$, Ar$^3$ may be substituted by one or more identical or different radicals R$^9$–R$^{14}$ as substituents
and the above proviso applies;
m is from 1 to 20, preferably 1, 2 or 3, particularly preferably 1;

X, Z are identical or different and are each a single bond, —O—, —S—, —SO—, —SO$_2$—, —CO—, —CO$^9$R$^{10}$—, —CR$^{11}$=CR$^{12}$—, —CHR$^{13}$—, —CHR$^{14}$—, —NR$^{15}$—;
Y is —O—, —S— or —NR$^{15}$—;
R$^9$–R$^{14}$ are identical or different and are each H, —CF$_3$, —Ph, —O—Ph, —S—Ph, —SO—Ph, —SO$_2$—Ph, F, Cl, Br, I, —CN or an alkyl group having from 1 to 22, preferably from 1 to 12, carbon atoms, where one or two nonadjacent CH$_2$ groups may also be replaced by —O—, —S—, —CO—, —CO—O—, —O—OC— or —Si(CH$_3$)$_2$—;
R$^{15}$ is as defined for R$^1$ and may be identical to or different from R$^1$;
n is 0, 1 or 2, preferably 0 or 1, particularly preferably 0.

Particular preference is given to polymers comprising repeating units of the formula (I) in which the symbols and indices have the following meanings:
Ar$^1$, Ar$^2$, Ar$^3$ are identical or different and are

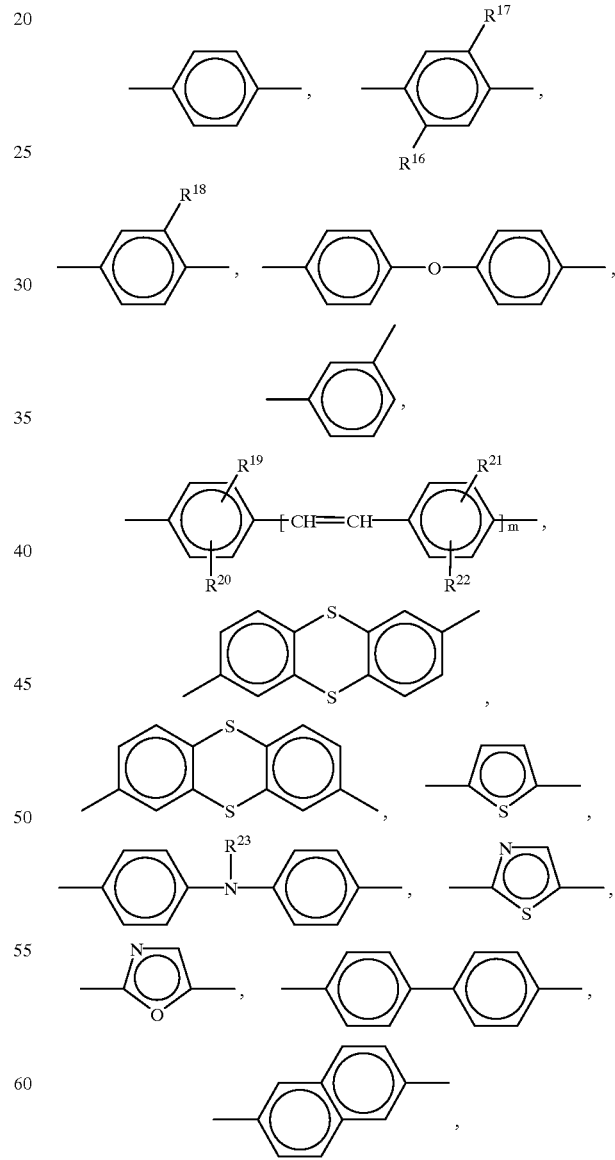

where the above proviso applies;
m is from 1 to 20, preferably 1, 2 or 3, particularly preferably 1;

$R^{16}$–$R^{23}$ are identical or different and are each F, Cl, $C_6$–$C_{10}$-aryl, a straight-chain or branched alkyl or alkoxy group having from 1 to 22, preferably from 1 to 12, carbon atoms and $R^{19-22}$ can also be H.

Very particular preference is given to the case where $Ar^1$, $Ar^2$ and $Ar^3$ are identical or different and are

[structures shown: benzophenone-type linker; dialkoxy-phenylene with $OR^{25}$ and $OR^{24}$; triphenylamine-type linker; phenylene; and methyl-substituted phenylene]

where the above proviso applies and
$R^{24}$, $R^{25}$ are identical or different and are straight-chain or branched alkyl groups having from 1 to 22, preferably from 1 to 12, carbon atoms.

In the polymers of the invention, it is preferred that:
$R^1=R^2$, $R^3=R^4=R^7=R^8$, $R^5=R^6$.

The polymers of the invention can be prepared by reacting a dicarbonyl compound of the formula (II), $$O=C(R^1)-Ar^1-C(R^2)=O \quad \text{(II)}$$

with at least two equivalents of an organophosphorus compound of the formula (III), $$Z_2P(=O)-CHR^3-Ar^2-CHR^4-P(=O)Z_2 \quad \text{(III)}$$

in the presence of a basic condensation agent, i.e. a base, and polymerizing the predominant intermediate of the formula (IV)

$$Z_2P(=O)-CHR^4-Ar^2-CR^3=CR^1-Ar^1-CR^2=CR^3-Ar^2-CHR^4-P(=O)Z_2 \quad \text{(IV)}$$

with a dicarbonyl compound of the formula (V)

$$O=C(R^5)-Ar^3-C(R^6)=O \quad \text{(V)}$$

in the presence of a base to give a polymer according to the invention comprising repeating units of the formula (I), where the symbols have the same meanings as in the formula (I) and Z are alkoxy radicals having from 1 to 16 carbon atoms, preferably ethoxy, or aryl radicals having from 6 to 10 carbon atoms, preferably phenyl.

This process is likewise a subject matter of the invention.

Similarly, it is naturally possible and subject matter of the invention to start from an organophosphorus compound of the formula (III) and react this with two equivalents of a carbonyl compound of the formula (II), which leads to an intermediate of the formula (IVa) which correspondingly bears carbonyl end groups and is polymerized with a further organophosphorus compound of the formula (IIIa) (with $R^5$ and $R^6$ instead of $R^3$ and $R^4$).

The condensation steps are carried out by action of a base, preferably a strong base, for example an alkoxide such as an alkali metal alkoxide or a hydride such as sodium hydride, preferably potassium tert-butoxide.

The polycondensation is advantageously carried out by initially charging a mixture of the starting components in a solvent and, under an inert gas atmosphere and while stirring, introducing preferably at least molar amounts of condensation agent in solution or suspension.

In another variant of the procedure, it is also possible for the condensation agent to be initially charged alone or together with the diketone (II) or (V) in a solvent and for the organophosphorus compound to be added. As solvents, preference is given to using hydrocarbons, particularly preferably aromatic hydrocarbons such as benzene, toluene or xylenes, or polar aprotic solvents, preferably amides such as N-methylpyrrolidone (NMP). The reaction temperature is preferably from 60 to 120° C. and the reaction time is from 5 to 20 hours.

The work-up can be carried out by addition of water, if desired an acid such as acetic acid and separating off the organic reaction phases. The condensation products obtained can be purified by extraction, e.g. using alcohols or acetic acid, or by precipitation from a solvent in a nonsolvent.

This preparative method is described in general in, for example, DD 84 272, Hörhold, H. -H.: Z. Chem. 1972, 12, 41; Hörhold, H. H-.; Bergmann, R.; Gottschaldt, J.; Drefahl, G.: Acta Chim. Acad. Sci. Hung. 81, 239; Hörhold, H. -H.; Bergmann, R.: Advances in the Chemistry of Thermally Stable Polymers, Warsaw, Polish Scientific Publishers 1977, 29–48; Hörhold, H. -H.; Helbig, M.: Makromol. Chem., Macromol. Symp., 1987, 12, 229 and Hörhold, H. -H.; Helbig, M.; Raabe, D.; Opfermann, J.; Scherf, U.; Stockmann, R.; Weiß, D.: Z. Chem. 1987, 27, 126.

The intermediate of the formula (IV) can be isolated by known methods with which those skilled in the art are familiar, but it is likewise preferred to react the compound of the formula (IV) with a further dicarbonyl compound (V) in situ.

It is likewise preferred to prepare compounds of the formula (IV) or (IVa) (with —$COR^4$ as end groups), by alternative synthetic methods, for example by reacting an organophosphorus compound of the formula (III) with two equivalents of a dicarbonyl compound protected at one end, for example as acetal or ketal, and subsequently removing the protective group. Further polymerization can then be carried out as described above.

The invention also provides the organic phosphorus compound of the formula (IV) or the dicarbonyl compound of the formula (IVa), which are likewise suitable for use as electroluminescence materials.

The invention likewise provides reaction products of the compound (IV) or (IVa) with monocarbonyl compounds or compounds containing one organophosphorus function, as are represented by the formula (VI), $$Ar^3-\underset{R^5}{\underset{|}{C}}=\underset{R^4}{\underset{|}{C}}-Ar^2-\underset{R^3}{\underset{|}{C}}=\underset{R^1}{\underset{|}{C}}-Ar^1-\underset{R^2}{\underset{|}{C}}=\underset{R^3}{\underset{|}{C}}-Ar^2-\underset{R^4}{\underset{|}{C}}=\underset{R^5}{\underset{|}{C}}-Ar^3 \quad (VI)$$

where the symbols have the meanings given for formula (I).

The starting compounds (II) and (III) are prepared by literature methods known per se, as are described in standard works on organic synthesis, e.g. Houben-Weyl, Methoden der Organischen Chemie, Georg-Thieme-Verlag, Stuttgart.

The preparation is carried out under reaction conditions which are known and suitable for the reactions in question. Use can also be made of variants which are known per se and are not described in more detail here.

The bis(diphenylphosphine oxides) or bis(phosphonic esters) required as condensation components can easily be obtained, for example, from the corresponding bis(halomethyl) compounds using the Michaelis-Arbusov reaction with ethyl diphenylphosphinite $(C_6H_5)_2P-O-C_2H_5$ or with triethyl phosphite.

Apart from primary phosphonates/phosphine oxides, secondary compounds are also suitable, in particular aromatic compounds.

The invention therefore also provides secondary bisphosphorus compounds of the formula (III), $$Z_2\underset{O}{\overset{\|}{P}}-CHR^3-Ar^2-CHR^4-\underset{O}{\overset{\|}{P}}Z_2 \quad (III)$$

where the symbols have the following meanings:
$Ar^2$ is a monocyclic or polycyclic, substituted or unsubstituted aryl or heteroaryl group which may be linked via one or more, preferably one, bridge or fused, preferably having from 2 to 100, particularly preferably from 2 to 50, very particularly preferably from 2 to 20, carbon atoms;
$R^3$, $R^4$, $R^5$ are identical or different and are each a hydrocarbon radical having from 1 to 22 carbon atoms, which may be unsubstituted or substituted, preferably by F, and may also contain heteroatoms, preferably O;
Z is an alkoxy radical having from 1 to 16 carbon atoms, preferably ethoxy, or an aryl radical having from 6 to 10 carbon atoms, preferably phenyl.
$R^3$ is preferably identical to $R^4$.

Further preference is given to compounds of the formula (III) in which the symbols have the following meanings:
$Ar^2$ is -continued

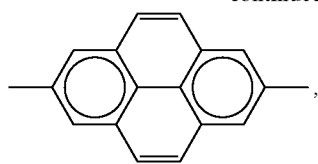 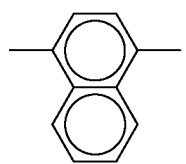

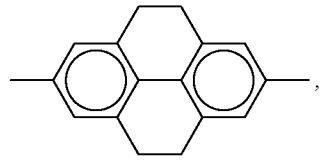 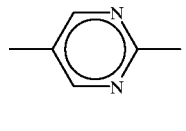

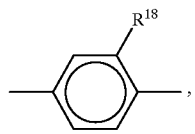

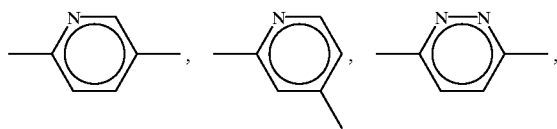

Ar² may here be substituted by one or more identical or different radicals R⁹–R¹⁴;

m is from 1 to 20, preferably 1, 2 or 3, particularly preferably 1;

X, Z are identical or different and are each a single bond, —O—, —S—, —SO—, —SO₂—, —CO—, —CR⁹R¹⁰—, —CR¹¹=CR¹²—, CHR¹³, —CHR¹⁴—, —NR¹⁵—;

Y is —O—, —S— or —NR¹⁵—;

R⁹–R¹⁴ are identical or different and are each H, —CF₃, —Ph, —O—Ph, —S—Ph, —SO—Ph, —SO₂—Ph, F, Cl, Br, I, —CN or an alkyl group having from 1 to 22, preferably from 1 to 12, carbon atoms, where one or two nonadjacent CH₂ groups may also be replaced by —O—, —S—, —CO—, —CO—O—, —O—OC— or —Si(CH₃)₂—;

R¹⁵ is H or a hydrocarbon radical having from 1 to 22 carbon atoms which may be unsubstituted or substituted, preferably by F, and may also contain heteroatoms, preferably O.

Particular preference is given to compounds of the formula III in which the symbols have the following meanings:

Ar² is:

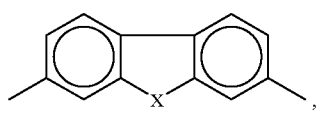

-continued

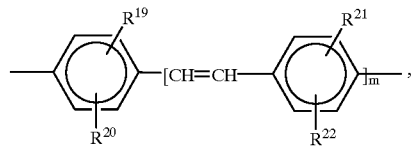

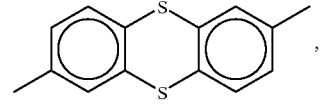

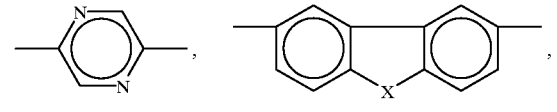

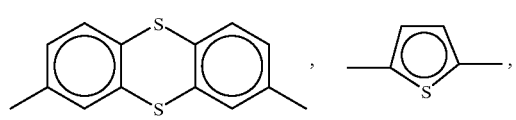

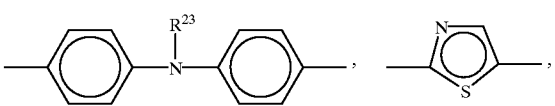

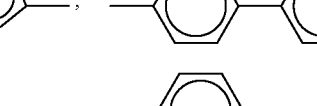

m is from 1 to 20, preferably 1, 2 or 3, particularly preferably 1;

R¹⁸–R²³ are identical or different and are each F, Cl, C₆–C₁₀-aryl, a straight-chain or branched alkyl or alkoxy group having from 1 to 22, preferably from 1 to 12, carbon atoms, R¹⁹⁻²² can also be H.

Very particular preference is given to compounds where Ar² is:

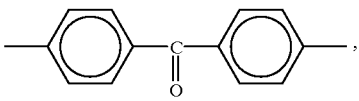

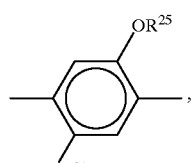

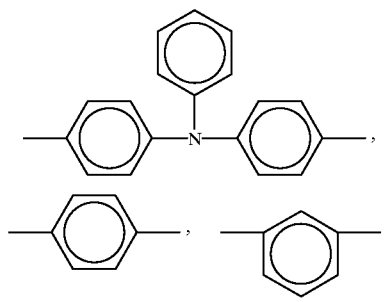

$R^{24}$, $R^{25}$ are identical or different straight-chain or branched alkyl groups having from 1 to 22, preferably from 1 to 12, carbon atoms.

The synthesis of aromatic diketones can be carried out, for example, by the known Friedel-Crafts reaction using $AlCl_3$ as catalyst, as is shown by way of example in Scheme 1 for three specific compounds.

where R is, for example, F or $CF_3$.

A further variant is the Grignard reaction of arylmagnesium bromides with dicyanoarylene shown by way of example in Scheme 2:

Scheme 2

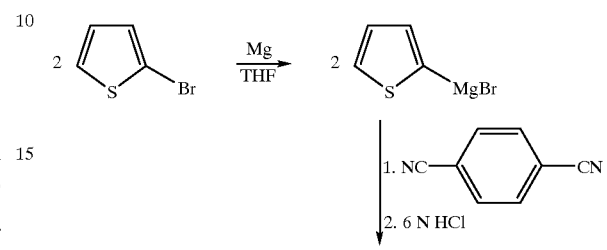

Scheme 1

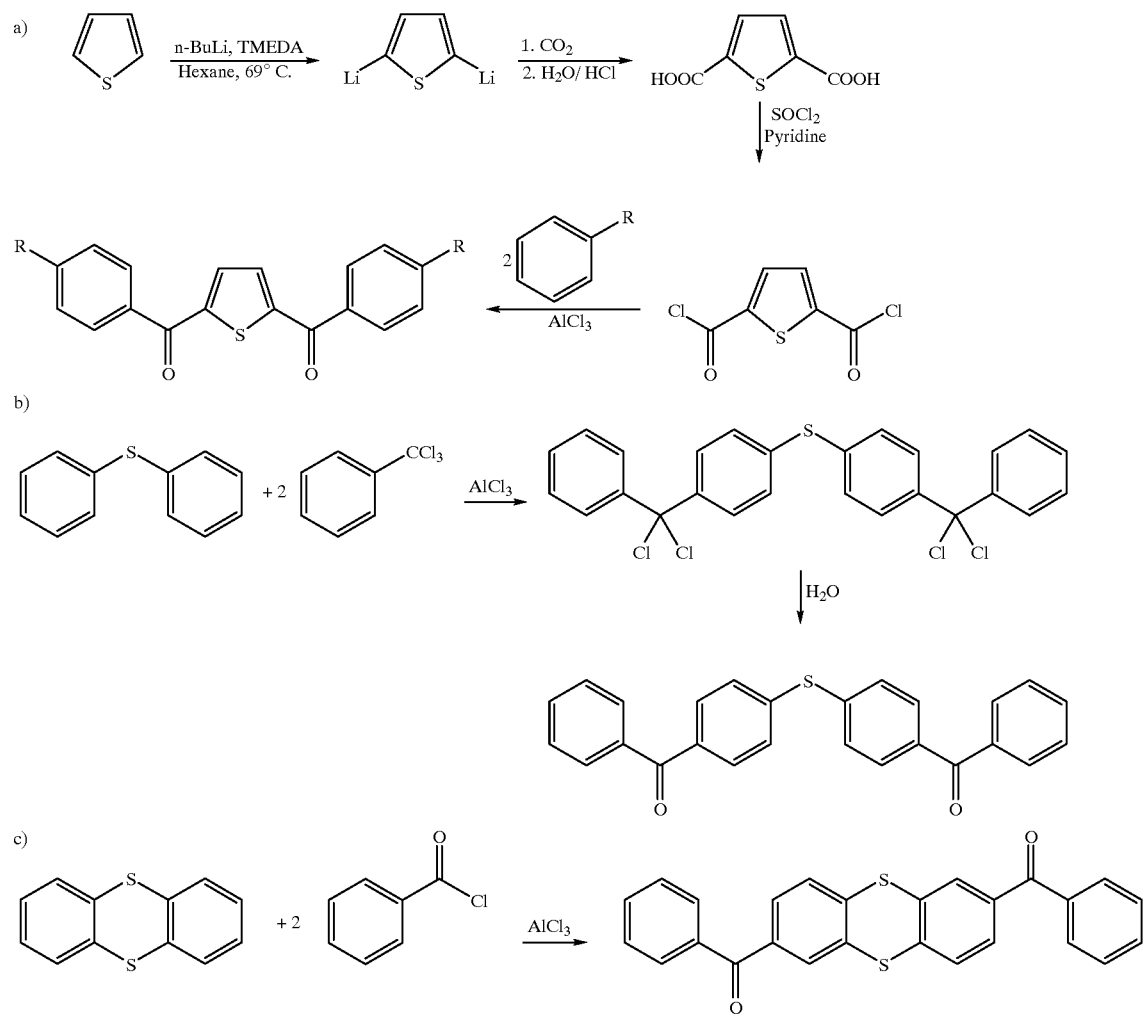

-continued

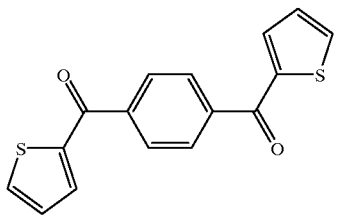

Bisaldehydes of the formula (II) can be synthesized by various types of reaction with which those skilled in the art are familiar.

Thus, for example, aldehydes can be obtained from bis-carboxylic acid derivatives by controlled reduction with reducing agents such as lithium trisalkoxyalanates or $H_2/Pd$ ("Rosenmund reduction"):

(see, for example, Fuson in Patai, "The Chemistry of the Carbonyl Group", Vol. 1, p. 211–232, Interscience, New York 1966)

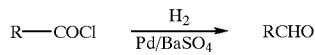

(see, for example, Tylander, "Catalytic Hydrogenation over Platinum Metals", p. 398–404, Academic Press, New York 1967).

Starting from bischloromethyl precursors, bisaldehydes can be obtained, for example, by the Sommelet reaction

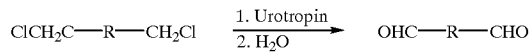

(see, for example, Angyal, Organic Reactions 1954, 8, 197); the Swern oxidation is likewise possible.

However, the parent aromatics are preferably subjected to an electrophilic aromatic substitution.

Numerous methods are known for this, for example the Gattermann-Koch reaction

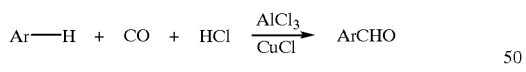

(see, for example, Crounse, Organic Reactions 1949, 5, 290–300); the Gattermann reaction:

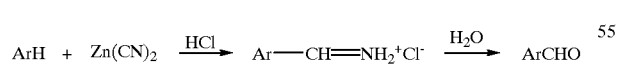

(see, for example, Truce, Organ. Reactions 1957, 9, 37–72); or the reaction of aromatics with dichloromethyl methyl ether:

(see, for example, Rieche et al., Chem. Ber. 1960, 93, 88 or Lewin et al., Org. Prep. Proced. Int. 1978, 10, 201).

Preference is given here to the Vilsmeier reaction, e.g. using DMF or N-methylformanilide:

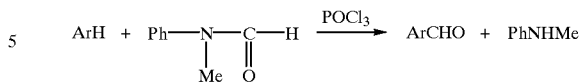

(see, for example, Jutz in Advances in Organic Chemistry, Vol. 9, Part 1, pp. 225–342, Böhme, Viche Eds. Interscience, New York 1976, or Jackson, J. Am. Chem. Soc. 1981, 103, 533).

Polymers comprising repeating units of the formula (I) are suitable as electroluminescence materials.

For the purposes of the invention, electroluminescence materials are materials which can be used as active layer in an electroluminescence device. Active layer means that the layer is capable of emitting light on application of an electric field (light-emitting layer) and/or that it improves the injection and/or transport of the positive and/or negative charges (charge injection layer or charge transport layer).

The invention therefore also provides for the use of a polymer comprising repeating units on the formula (I) as electroluminescence material.

For use as electroluminescence materials, the polymers comprising structural units of the formula (I) are applied in the form of a film to a substrate, in general by known methods with which those skilled in the art are familiar, e.g. dipping or spin coating.

The invention therefore also provides a process for producing an electroluminescence material, which comprises a) reacting a dicarbonyl compound of the formula (II)

(II)

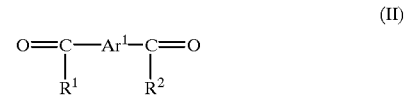

with at least two equivalents of an organophosphorus compound of the formula (III)

(III)

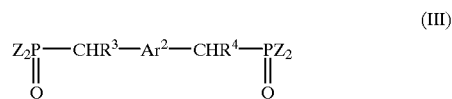

in the presence of a basic condensation agent, b) polymerizing the predominant intermediate of the formula (IV)

(IV)

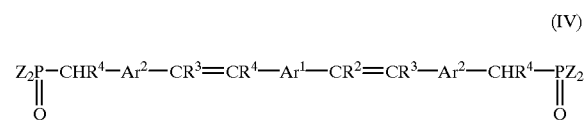

with a dicarbonyl compound of the formula (V)

(V)

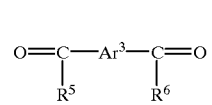

in the presence of a base to give a polymer according to the invention comprising repeating units of the formula (I), where the symbols have the same meanings as in the formula (I) and Z are alkoxy radicals having from 1 to 16 carbon atoms, preferably ethoxy, or aryl radicals having from 6 to 10 carbon atoms, preferably phenyl, and c) applying the resulting polymer comprising repeating units of the formula (I) in the form of a film to a substrate which, if desired, also comprises further layers.

The invention also provides an electroluminescence device comprising one or more active layers, where at least one of these active layers comprises one or more polymers according to the invention. The active layer can be, for example, a light-emitting layer and/or a transport layer and/or a charge injection layer.

The general structure of such electroluminescence devices is described, for example, in U.S. Pat. No. 4,539,507 and U.S. Pat. No. 5,151,629. Polymer-containing electroluminescence devices are described, for example, in WO-A 90/13148 and EP-A 0 443 861.

They usually comprise an electroluminescent layer between a cathode and an anode, with at least one of the electrodes being transparent. In addition, one or more electron injection layers and/or electron transport layers may be incorporated between the electroluminescent layer and the cathode and/or one or more hole injection layers and/or hole transport layers may be incorporated between the electroluminescent layer and the anode. As cathode, preference is given to metals or metallic alloys, e.g. Ca, Mg, Al, In, Mg/Ag. As anode, it is possible to use metals, e.g. Au, or other materials having metallic conduction, for example oxides such as ITO (indium oxide/tin oxide), on a transparent substrate, e.g. of glass or a transparent polymer.

In operation, the cathode is placed at a negative potential relative to the anode. Electrons from the cathode are then injected into the electron injection layer/electron transport layer or directly into the light-emitting layer. At the same time, holes from the anode are injected into the hole injection layer/hole transport layer or directly into the light-emitting layer.

The charge carriers which have been injected move toward one another through the active layers under the action of the applied voltage. This leads to electron/hole pairs at the interface between charge transport layer and light-emitting layer or within the light-emitting layer and these pairs recombine with emission of light.

The color of the light which is emitted can be varied by means of the materials used as light-emitting layer.

Electroluminescence devices are employed, for example, as self-illuminating display elements such as control lamps, alphanumeric displays, signs, and in optoelectronic couplers.

The invention is illustrated by the examples without being restricted thereby.

Abbreviations used have the following meanings:

$T_g$: Glass transition temperature, measured by means of differential scanning calorimetry (DSC)

$M_n$: Number average molecular weight

VPO: Vapor Pressure Osmometry (see, for example, Cherdron, Kern, Braun, Praktikum der Makromolekularen Chemie)

GPC: Gel permeation chromatography, standard: polystyrene

MS: Mass spectrometry

UV/VIS: UV/VIS spectroscopy

EXAMPLE 1

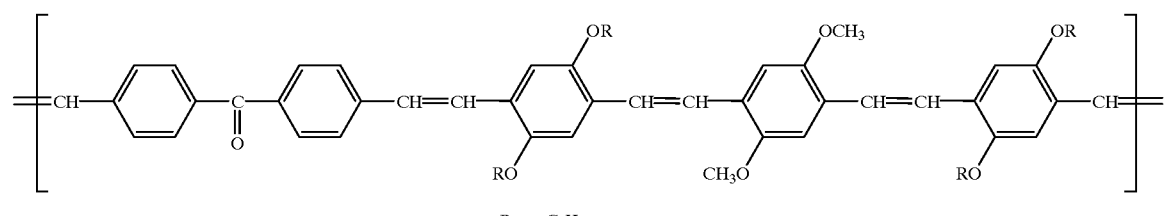

R = n-C$_8$H$_{17}$

| | |
|---|---|
| 2,5-dioctoxy-p-xylylenebis(diethyl phosphonate) | 6.53 g (0.010 mol) |
| 2,5-dimethoxyterephthalaldehyde | 1.00 g (0.005 mol) |
| 4,4'-diformylbenzophenone | 1.22 g (0.005 mol) |
| Potassium tert-butoxide | 1.15 g (0.010 mol) 1st portion |
| | 1.15 g (0.010 mol) 2nd portion |

The bisphosphonate (0.01 mol) and the dimethoxyterephthalaldehyde (0.005 mol) are heated to 80° C. in 150 ml of toluene under protective gas and while stirring. The first portion of potassium tert-butoxide (0.01 mol) is then added to form the trimeric precursor.

The solution becomes red and has an orange fluorescence. After two minutes, the diformylbenzophenone (0.005 mol) is added in solid form and the mixture is heated to the boiling point. The remaining potassium tert-butoxide (0.01 mol) is then added in solid form, with the reaction mixture foaming vigorously and becoming viscous. The color of the solution darkens and the fluorescence becomes more intense. The mixture is stirred for another hour at the boiling point and is then poured into 500 ml of methanol. This gives deep red flocs which are filtered off with suction. After drying, the product is dissolved in chloroform and precipitated in isopropanol to give a bright red powder in a yield of 46%.

| | |
|---|---|
| Molar mass (GPC, PS standard): | $M_n$ = 4600 |
| | $M_w$ = 14,100 |
| Glass transition temperature | $T_g$ = 41° C. |

| | |
|---|---|
| (DSC): | |
| UV/VIS: | $\lambda_{MAX}$ = 452 nm with broad shoulder, $\lambda_{0.1MAX}$ 565 nm, $Eg^{OPT}$ = 2.19 Ev, Ig $\epsilon$ = 4.7 |
| Fluorescence: | $\lambda_{MAX,EXC}$ = 450 nm, $\lambda_{MAX\ EM}$ = 535 nm, $Eg^{0-0}$ = 2.48 eV, $\Phi_{PL}$ = 34% |
| Electrochemistry: | $E^{OX1}$ = from 0.70 V vs. Ag/AgCl (reversible), very broad $E^{Red1}$ = 1.24 V vs. Ag/AgCl (reversible) |
| IR spectrum: | CH=CH - trans 968 cm$^{-1}$ |

EXAMPLE 2

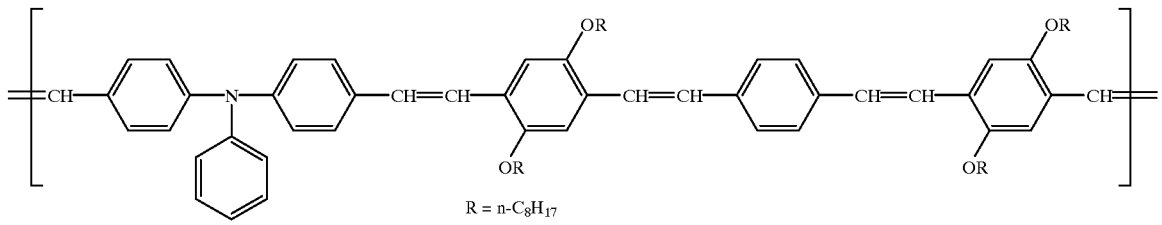

R = n-C$_8$H$_{17}$

| | |
|---|---|
| 2,5-dioctoxy-p-xylylenebis(diethyl phosphonate) | 2.00 g (0.0031 mol) |
| Terephthalaldehyde | 0.21 g (0.0015 mol) |
| 4,4'-diformyltriphenylamine | 0.47 g (0.0015 mol) |
| Potassium tert-butoxide | 0.35 g (0.0031 mol) = 1st portion |
| | 0.35 g (0.0031 mol) = 2nd portion |

The bisphosphonate (3.1 mmol) and terephthalaldehyde (1.5 mmol) are heated to 80° C. in 150 ml of toluene under protective gas and while stirring. The first portion of potassium tert-butoxide (3.1 mmol) is then added, forming the trimeric precursor. The solution becomes yellowish and has a light green fluorescence. After two minutes, the amine aldehyde (1.5 mmol) is added in solid form and the mixture is heated to the boiling point. The remaining potassium tert-butoxide (3.1 mmol) is then added in solid form, with the reaction mixture foaming vigorously and becoming viscous. The color of the solution darkens and the fluorescence becomes more intense. The mixture is stirred for another hour at the boiling point, the solvent is taken off, the residue is taken up in chloroform and precipitated in methanol. This gives orange flocs which are filtered off with suction and are extracted with methanol for another four hours. Drying gives a bright orange powder in a yield of 49%.

| | |
|---|---|
| Molar mass (GPC, PS standard): | $M_n$ = 10,500 $M_w$ = 18,700 |
| Glass transition temperature (DSC): | $T_g$ = 46° C. |
| UV/VIS: | $\lambda_{MAX}$ = 452 nm, Ig $\epsilon$ = 4.8 |
| Fluorescence: | $\lambda_{MAX,EXC}$ = 449 nm, $\lambda_{MAX\ EM}$ = 509 nm, $Eg^{0-0}$ = 2.53 eV, $\Phi_{PL}$ = 66% |
| Electrochemistry: | Oxidation potential $E^{OX1}$ = 0.71 V vs. Ag/AgCl (reversible), by cyclovoltammetry) |
| IR spectrum: | CH=CH - trans 960 cm$^{-1}$ |

EXAMPLE 3

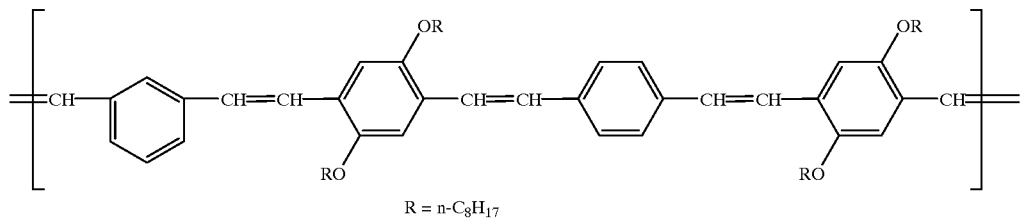

R = n-C$_8$H$_{17}$

| | |
|---|---|
| 2,5-dioctoxy-p-xylylenebis(diethyl phosphonate) | 8.00 g |
| Terephthalaldehyde | 0.84 g |
| Isophthalaldehyde | 0.84 g |
| Potassium tert-butoxide | 1.41 g (1st portion) |

-continued

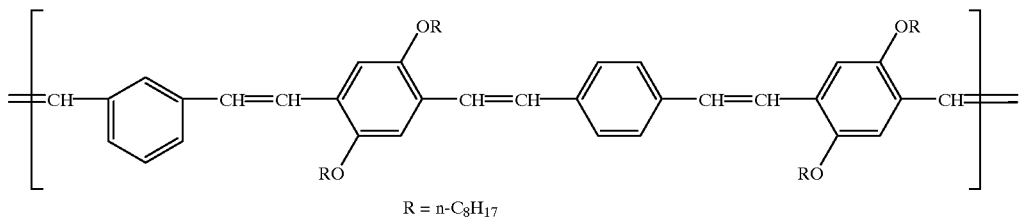

R = n-C₈H₁₇

| | |
|---|---|
| | 1.41 g (2nd portion) |

Bisphosphonate and isophthalaldehyde are heated to 100° C. in 150 ml of toluene under protective gas and while stirring. The first portion of potassium tert-butoxide is then added to form the trimeric precursor. The solution becomes yellowish and has a blue fluorescence. After two minutes, the terephthalaldehyde is added in solid form and the mixture is heated to the boiling point. The remaining potassium tert-butoxide is then added in solid form, with the reaction mixture foaming vigorously and becoming viscous. The color of the solution becomes darker and the fluorescence becomes more intense. The mixture is stirred for another hour at the boiling point and is then poured into 500 ml of methanol. This gives orange flocs which are filtered off with suction. After drying, the residue is taken up in chloroform, precipitated in isopropanol and extracted with methanol for 5 hours. This gives a bright orange powder in a yield of 65% (3.8 g).

| Molar mass (VPO): | $M_n$ = 11,300 |
|---|---|
| UV/VIS: | $\lambda_{MAX}$ = 421 nm, shoulder at 452 nm, lg $\epsilon$ = 477 |
| Fluorescence: | $\lambda_{MAX,EXC}$ = 420 nm, $\lambda_{MAX\ EM}$ = 507 nm, shoulder at 540 nm |
| Electrochemistry: | $E^{OX1}$ = 0.80 V vs. Ag/AgCl (reversible), very broad |
| IR spectrum: | CH=CH - trans 964 cm$^{-1}$ |

The bisphosphonate (7.4 mmol) and the dimethoxyterephthalaldehyde (3.7 mmol) are heated to 80° C. in 150 ml of toluene under protective gas and while stirring. The first portion of potassium tert-butoxide (7.4 mmol) is then added to form the trimeric precursor. The solution becomes orange-red and has a yellow fluorescence. After two minutes, the amine aldehyde (3.7 mmol) is added in solid form and the mixture is heated to the boiling point. The remaining potassium tert-butoxide (7.4 mmol) is then added in solid form, with the reaction mixture foaming vigorously and becoming viscous. The color of the solution darkens and the fluorescence becomes more intense. The mixture is stirred for another hour at the boiling point, the solvent is taken off, the residue is taken up in chloroform and is precipitated in methanol. This gives red flocs which are filtered off with suction and are extracted with methanol for another four hours. Drying gives a bright red powder in a yield of 45%.

| Molar mass (GPC, PS standard): | $M_n$ = 4100, $M_w$ = 6300 |
|---|---|
| UV/VIS: | $\lambda_{MAX}$ = 450 nm, $\lambda_{MAX}$ = 537 nm, $Eg^{OPT}$ = 2.32, lg $\epsilon$ = 4.8 |
| Fluorescence: | $\lambda_{MAX,EXC}$ = 440 nm, $\lambda_{MAX\ EM}$ = 527 nm, $Eg^{0-0}$ = 2.54 eV, $\Phi_{PL}$ = 45% |
| Electrochemistry: | $E^{OX1}$ = 0.78 V (reversible), $E^{OX2}$ = 1.38 V |
| IR spectrum: | CH=CH-trans 965 cm$^{-1}$ |

EXAMPLE 4

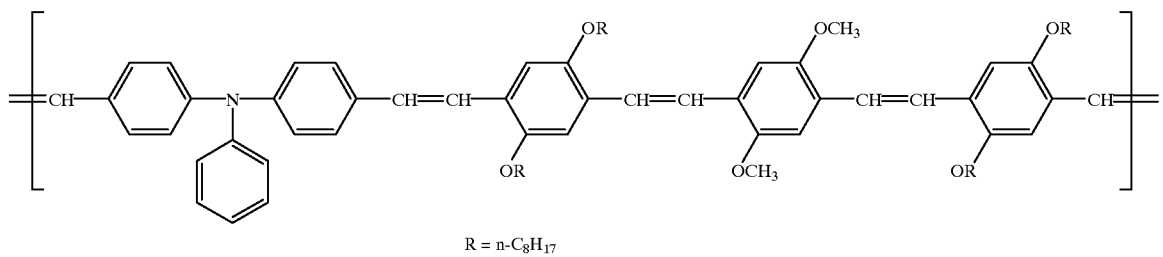

R = n-C₈H₁₇

| | |
|---|---|
| 2,5-dioctoxy-p-xylylenebis(diethyl phosphonate) Ro 14 | 4.70 g (0.0074 mol) |
| 2,5-dimethoxyterephthalaldehyde | 0.72 g (0.0037 mol) |
| 4,4'-diformylphenylamine | 1.11 g (0.0037 mol) |
| Potassium tert-butoxide | 0.83 g (0.0074 mol) = 1st portion |
| | 0.83 g (0.0074 mol) = 2nd portion |

EXAMPLE 5

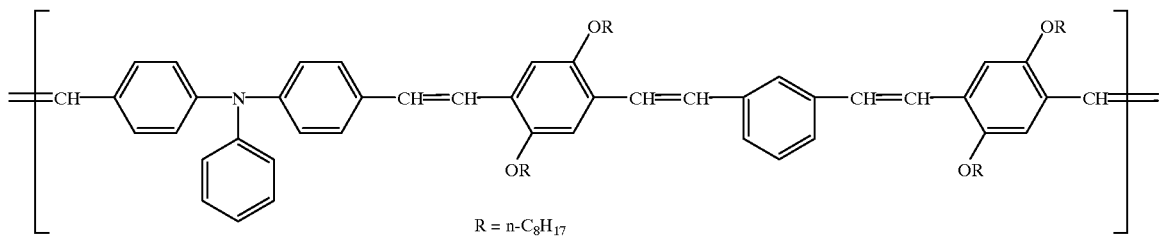

| | |
|---|---|
| 2,5-dioctoxy-p-xylylenebis(diethyl phosphonate) | 2.00 g (0.0031 mol) |
| Isophthalaldehyde | 0.21 g (0.0015 mol) |
| 4,4'-diformyltriphenylamine | 0.47 g (0.0015 mol) |
| Potassium tert-butoxide | 0.35 g (0.0031 mol) (1st portion) |
| | 0.35 g (0.0031 mol) (2nd portion) |

The bisphosphonate and the isophthalaldehyde are heated to 80° C. in 150 ml of toluene under protective gas and while stirring. The first portion of potassium tert-butoxide is then added to form the trimeric precursor. The solution becomes yellowish and has a strong blue fluorescence. After two minutes, the amine aldehyde is added in solid form and the mixture is heated to the boiling point. The remaining potassium tert-butoxide is then added in solid form, with the reaction mixture foaming vigorously and becoming viscous. The color of the solution darkens and the fluorescence becomes more intense. The mixture is stirred for another hour at the boiling point, the solvent is taken off, the residue is taken up in chloroform and is precipitated in methanol. This gives yellow flocs which are filtered off with suction and extracted with methanol for another four hours. Drying gives a bright yellow powder in a yield of 64%.

| | |
|---|---|
| Molar mass (VPO): | $M_n$ = 7700 |
| UV/VIS: | $\lambda_{MAX}$ = 420 nm (shoulder at 460 nm) |
| Fluoroescence: | $\lambda_{MAX,EXC}$ = 417 nm, $\lambda_{MAX\ EM}$ = 493 nm, $\Phi_{Fluo}$ = 65% |
| Electrochemistry: | $E^{OX1}$ = 0.72 V vs. Ag/AgCl |

EXAMPLE 6

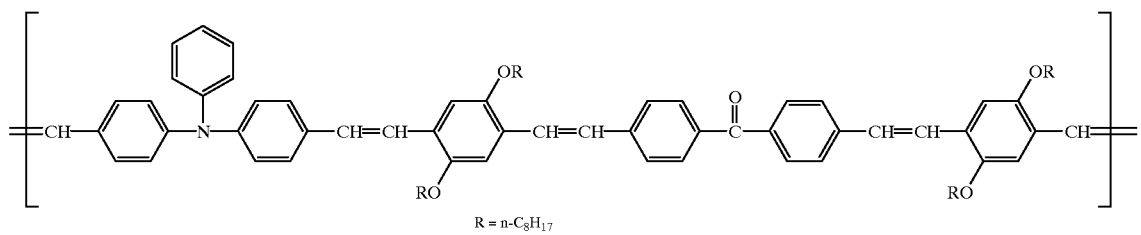

| | |
|---|---|
| 2,5-dioctoxy-p-xylylenebis(diethyl phosphonate) | 5.32 g (0.0083 mol) |
| 4,4'-diformylbenzophenone | 1.00 g (0.0041 mol) |
| 4,4'-diformyltriphenylamine | 1.26 g (0.0041 mol) |
| Potassium tert-butoxide | 0.94 g (0.0082 mol) (1st portion) |
| | 0.94 g (0.0083 mol) (2nd portion) |

The bisphosphonate (0.0083 mol) and the diformyltriphenylamine (0.0041 mol) are heated to 80° C. in 150 ml of toluene under protective gas and while stirring. The first portion of potassium tert-butoxide (0.0083 mol) is then added to form the trimeric precursor. The solution becomes yellowish and has a green fluorescence. After two minutes, the diformylbenzophenone (0.0041 mol) is added in solid form and the mixture is heated to the boiling point. The remaining potassium tert-butoxide (0.0083 mol) is then added in solid form, with the reaction mixture foaming vigorously and becoming viscous. The color of the solution darkens and the fluorescence becomes more intense. The mixture is stirred for another hour at the boiling point and is then poured into 500 ml of methanol. This gives orange flocs which are filtered off with suction. After drying, the product is taken up in chloroform and precipitated in isopropanol to give a bright orange powder in a yield of 49%.

8.8 g of bisphosphonate together with 5.7 g of the protected aldehyde are dissolved in 100 ml of toluene and heated to 80–100° C. under protective gas. The potassium tert-butoxide is then added in one portion, with the reaction mixture foaming vigorously. The strongly fluorescent solution is refluxed for two hours while stirring and is then hydrolyzed using 100 ml of 10% strength hydrochloric acid. The organic phase is separated off, washed with water and then evaporated to dryness. The yellow-orange solid is dissolved in hot ethanol and admixed with 20 ml of water and a spatula tip of p-toluenesulfonic acid. The mixture is then refluxed for another 20 minutes, forming a clear orange solution. The compound crystallizes out on careful cooling (orange needles, $T_m$=118° C., yield: 76%).

| Molar mass (GPC, PS standard): | $M_n$ = 9200 $M_w$ = 20,600 |
|---|---|
| Glass transition temperature (DSC): | $T_g$ = 57° C. |
| UV/VIS: | $\lambda_{MAX}$ = 439 nm, $\lambda_{MAX}$ = 495 nm, $Eg^{OPT}$ = 2.50 eV, Ig ε = 4.95 |
| Fluorescence: | $\lambda_{MAX,EXC}$ = 449 nm, $\lambda_{MAX\ EM}$ = 496 nm, $Eg^{0-0}$ = 2.57 eV, $\Phi_{PL}$ = 28% |
| Electrochemistry: | $E^{OX1}$ = 0.73 V vs. Ag/AgCl (reversible) $E^{OX2}$ = 1.08 V vs. Ag/AgCl (reversible) $E^{Red1}$ = 1.50 V vs. Ag/AgCl (reversible) |
| IR spectrum: | CH=CH - trans 960 cm$^{-1}$ |
| Single layer of ITO/Ca U = 16.9 V 153 Cd/m$^2$ | 100 nm of polymer Eff. = 0.038% external |

| $C_{40}H_{50}O_4$ (594.76) | calc. C: 80.77 | calc. H: 8.47 |
|---|---|---|
| | found C: 80.62 | found H: 8.42 |

| Molar mass by MS: | m/e 594 |
|---|---|
| Electrochemistry: | $E^{OX1}$ = + 1.18 V vs. Ag/AgCl (reversible) $E^{Red1}$ = 1.46 V vs. Ag/AgCl (reversible) |
| UV/VIS: | $\lambda_{MAX}$ = 420 nm, Ig ε = 4.2 |
| Fluorescence: | $\lambda_{MAX}$, (emission) = 485 nm, $\Phi_{PL}$ = 71% |

EXAMPLE 7

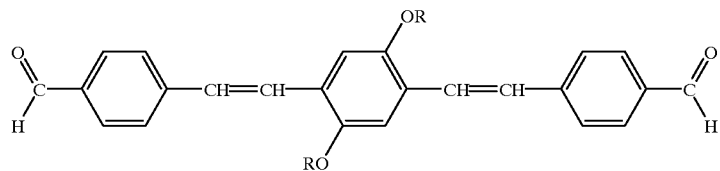

1,4-Bis(4-formylstyryl)-2,5-dioctoxybenzene(R = n-$C_8H_{17}$)

| 2,5-dioctoxy-p-p-xylylenebis(diethyl phosphonate) | 8.8 g (13.8 mmol) |
|---|---|
| 4-di(ethoxymethyl)benzaldehyde | 5.7 g (27.7 mmol) |
| Potassium tert-butoxide | 3.1 g (27.7 mmol) |

EXAMPLE 8

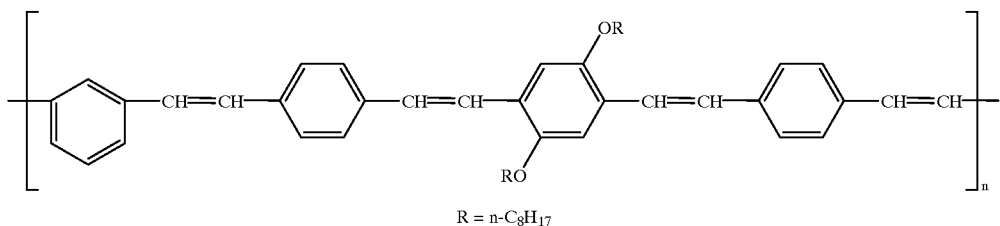

R = n-C$_8$H$_{17}$

| | |
|---|---|
| 1,4-bis(4-formylstyryl)-2,5-dioctoxybenzene | 2.00 g (3.3 mmol) |
| m-xylylenebis(diethyl phosphonate) | 1.27 g (3.3 mmol) |
| Potassium tert-butoxide | 0.75 g (6.6 mmol) |

2.00 g of the trimeric precursor as described in Example 7 together with 1.27 g of bisphosphonate are heated to 100° C. in 50 ml of toluene under protective gas and while stirring. The potassium tert-butoxide is added in solid form in one portion, with the mixture foaming vigorously and becoming viscous. The mixture is refluxed for another two hours and is then poured into 500 ml of methanol. This results in precipitation of the polymer in large yellow flocs. The crude product is then filtered off with suction and subsequently extracted with methanol for four hours (yield: 80% after drying under reduced pressure).

EXAMPLE 9

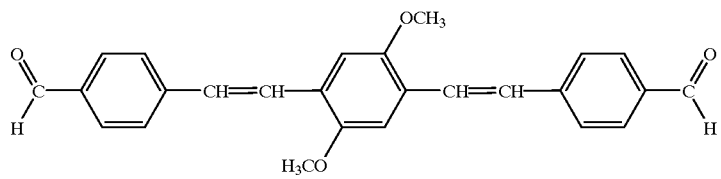

1,4-(Bis-(4-formylstyryl)-2,5-dimethoxybenzene

| | |
|---|---|
| 4-(diethoxymethyl)benzaldehyde | 8.88 g (42.6 mmol) |
| 2,5-dimethoxy-p-xylylenebis(diethyl phosphonate) | 9.34 g (21.3 mmol) |
| Potassium tert-butoxide | 5.97 g (53.2 mmol) |

4-(Diethoxymethyl)benzaldehyde (8.88 g; 42.6 mmol) and the 2,5-dimethoxy-p-xylylenebis(diethyl phosphonate) (9.34 g; 21.3 mmol) are weighed into a dry 500 ml three-neck flask provided with magnetic stirrer and reflux condenser and are admixed with 500 ml of toluene. The apparatus is flushed with argon and the reaction mixture is subsequently heated to an oil bath temperature of from 100 to 110° C., forming a clear solution. The potassium tert-butoxide is then carefully added under argon, with the reaction mixture foaming slightly. After ½ hour, the mixture becomes so viscous that another 50 ml of toluene are added. It is then stirred for 2 hours at the above oil bath temperature. After the reaction time has expired, the mixture is hydrolyzed using dilute acetic acid. The phases are separated and the toluene phase is shaken a number of times with dilute acetic acid. The organic phase is subsequently washed six times with 100 ml of water. The toluene phase is dried using a water separator. After filtration, the filtrate is evaporated on a rotary evaporator, resulting in crystallization of the product. This is filtered off with suction, washed with n-hexane and dried at 60° C. under reduced pressure. 2.1 g (25%) of orange powder are obtained.

| | | | |
|---|---|---|---|
| C$_{26}$H$_{22}$O$_4$ (398.44) | calc. C: 78.37 | | H: 5.57 |
| | found C: 78.12 | | H: 5.86 |
| $\lambda_{max}$: | | 419 nm | |
| $\lambda_{max\,0.1}$: | | 472 nm | |

-continued

| | |
|---|---|
| IG$\epsilon_{max}$: | 4.69 |
| E$_{opt}$: | 2.62 eV |

Fluorescence spectrum (recorded in solution; solvent: dioxane)

| | |
|---|---|
| $\lambda_{max}$: | 420 nm |
| $\lambda_{am}$: | 484 nm |
| $\lambda_{0-0}$: | 460 nm |
| E$_{0-0}$: | 2.69 eV |
| $\Phi_{PL}$: | 76% |

EXAMPLE 10

[Structure of polymer showing OCH3, H3CO substituted phenylene-vinylene units with OC6H5 and OC5H6 substituents]

| | |
|---|---|
| 1,4-bis(4-formylstyryl)-2,5-dimethoxybenzene | 1.51 g (3.79 mmol) |
| Benzene-1,4-bis(diethyl 4-phenoxyphenylmethylphosphonate) | 2.71 g (3.79 mmol) |
| Potassium tert-butoxide | 1.28 g (11.4 mmol) |

Bisaldehyde (1.51 g; 3.79 mmol) and benzene-1,4-bis(diethyl 4-phenoxyphenylmethylphosphonate) (2.71 g; 3.79 mmol) are weighed into a dry 250 ml two-neck flask provided with magnetic stirrer and reflux condenser and are admixed with 70 ml of absolute toluene. The apparatus is flushed with argon and the reaction mixture is subsequently heated to an oil bath temperature of from 130 to 150° C., forming a clear solution. The potassium tert-butoxide is then carefully added under argon, with the reaction mixture foaming slightly. After addition of the potassium tert-butoxide, the mixture is stirred for 3–4 hours at the above oil bath temperature. After the reaction time has expired, the mixture is hydrolyzed using 50 ml of 10% strength acetic acid. The phases are separated and the organic phase is washed a number of times with water. The toluene phase is subsequently dried using a water separator. After filtration, the filtrate is evaporated on a rotary evaporator and precipitated in 500 ml of methanol. The yellow-orange precipitate is filtered off with suction and extracted with methanol and subsequently with cyclohexane. Drying under reduced pressure at from 100 to 150° C. gives 1.86 g (55%) of polymer.

| | |
|---|---|
| $M_n$ (GPC) | 8210 g mol$^{-1}$ |
| $M_w$ (GPC) | 29,800 g mol$^{-1}$ |
| $M_w/M_n$ | 3.63 |
| $T_g$ | >150° C. |
| $\lambda_{max}$: | 432 nm |
| $\lambda_{max\ 0.1}$: | 490 nm |
| $IG\epsilon_{max}$: | 4.89 |
| $E_{opt}$: | 2.53 eV |

What is claimed is:

1. A poly(arylene-vinylene) terpolymer comprising repeating units of the formula (I),

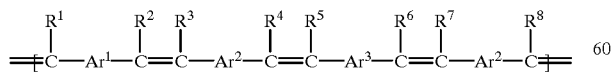
(I)

where the symbols have the following meanings:
Ar$^1$, Ar$^2$, Ar$^3$ are identical or different and are monocyclic or polycyclic, substituted or unsubstituted aryl or heteroaryl groups which may be linked via one or more bridges or be fused, R$^1$, R$^2$, R$^3$, R$^4$, R$^5$, R$^6$, R$^7$, R$^8$ are identical or different and are each H or a hydrocarbon radical having from 1 to 22 carbon atoms which may be substituted and may also contain heteroatoms;

with the proviso that =CR$^1$—Ar$^1$—CR$^2$=, =CR$^3$—Ar$^2$—CR$^4$= and CR$^5$—Ar$^3$—CR$^6$= are each different from one another.

2. A polymer as claimed in claim 1 consisting of repeating units of the formula (I).

3. A polymer as claimed in claim 1 having from 2 to 1000 repeating units of the formula (I).

4. A polymer as claimed in claim 1, wherein the symbols in the formula (I) have the following meanings: Ar$^1$, Ar$^2$, Ar$^3$ are identical or different and are

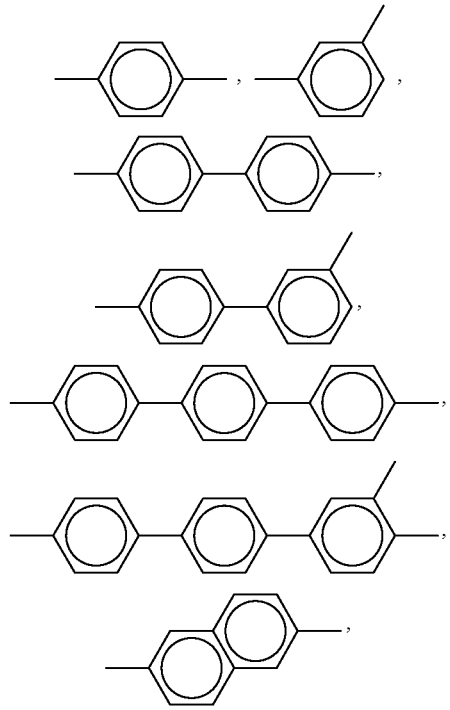

-continued

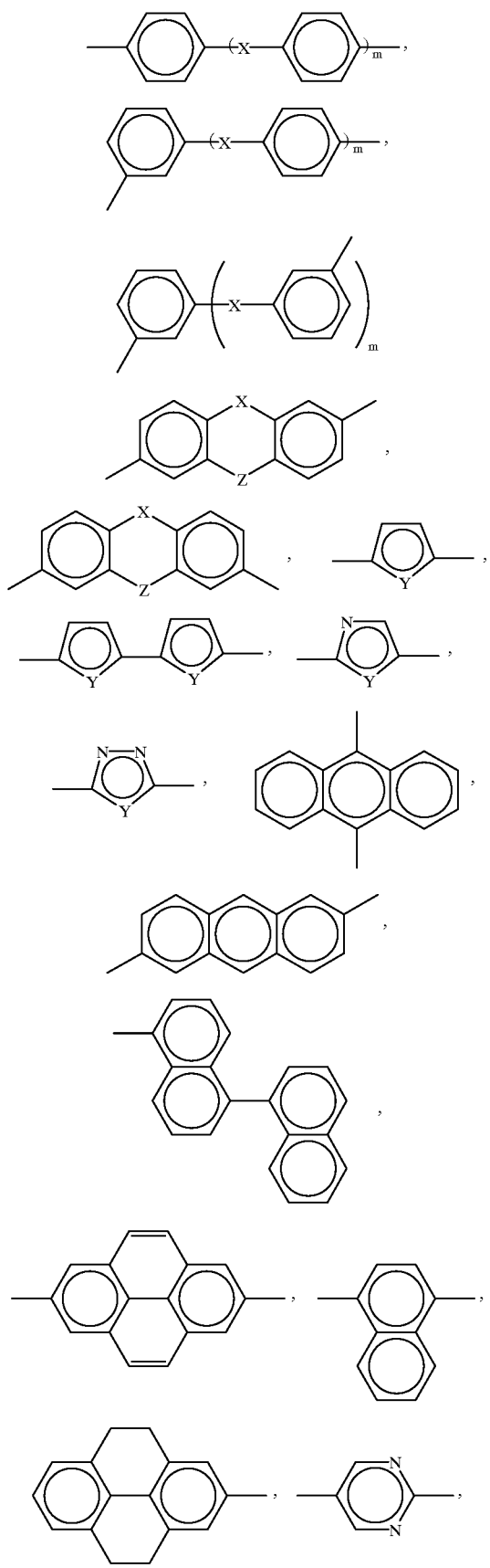

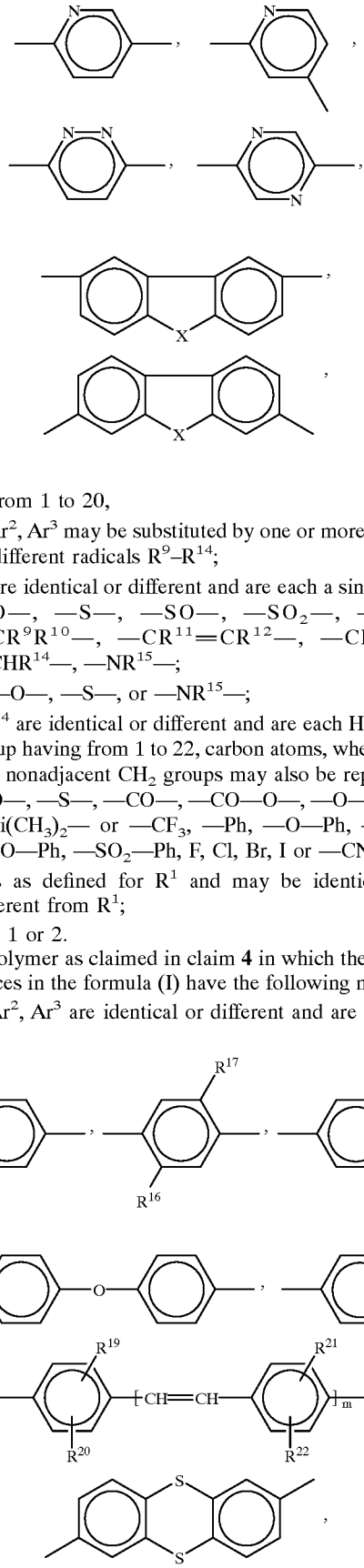

m is from 1 to 20,

Ar$^1$, Ar$^2$, Ar$^3$ may be substituted by one or more identical or different radicals R$^9$–R$^{14}$;

X, Z are identical or different and are each a single bond, —O—, —S—, —SO—, —SO$_2$—, —CO—, —CR$^9$R$^{10}$—, —CR$^{11}$=CR$^{12}$—, —CHR$^{13}$—, —CHR$^{14}$—, —NR$^{15}$—;

Y is —O—, —S—, or —NR$^{15}$—;

R$^9$–R$^{14}$ are identical or different and are each H, an alkyl group having from 1 to 22, carbon atoms, where one or two nonadjacent CH$_2$ groups may also be replaced by —O—, —S—, —CO—, —CO—O—, —O—OC— or —Si(CH$_3$)$_2$— or —CF$_3$, —Ph, —O—Ph, —S—Ph, —SO—Ph, —SO$_2$—Ph, F, Cl, Br, I or —CN;

R$^{15}$ is as defined for R$^1$ and may be identical to or different from R$^1$;

n is 0, 1 or 2.

5. A polymer as claimed in claim 4 in which the symbols and indices in the formula (I) have the following meanings:

Ar$^1$, Ar$^2$, Ar$^3$ are identical or different and are

-continued

[structures shown: thianthrene derivative, thiophene, triarylamine with $R^{23}$, thiazole, oxazole, biphenyl, naphthalene]

m is from 1 to 20, $R^{16}$–$R^{23}$ are identical or different and are each F, Cl, $C_6$–$C_{10}$-aryl, a straight-chain or branched alkyl or alkoxy group having from 1 to 22, carbon atoms and $R^{19-22}$ can also be H.

6. A process for preparing a polymer as claimed in claim 1 which comprises reacting a dicarbonyl compound of the formula (II), $$O{=}C(R^1){-}Ar^1{-}C(R^2){=}O \qquad (II)$$

with at least two equivalents of an organophosphorus compound of the formula (III), $$Z_2\overset{O}{\underset{\|}{P}}{-}CHR^3{-}Ar^2{-}CHR^4{-}\overset{O}{\underset{\|}{P}}Z_2 \qquad (III)$$

in the presence of a base, and polymerizing the resulting intermediate of the formula (IV)

$$Z_2\overset{O}{\underset{\|}{P}}{-}CHR^4{-}Ar^2{-}CR^3{=}CR^4{-}Ar^1{-}CR^2{=}CR^3{-}Ar^2{-}CHR^4{-}\overset{O}{\underset{\|}{P}}Z_2 \qquad (IV)$$

with a dicarbonyl compound of the formula (V)

$$O{=}C(R^5){-}Ar^3{-}C(R^6){=}O \qquad (V)$$

in the presence of a base to give a polymer comprising repeating units of the formula (I), where the symbols have the same meanings as in the formula (I) in claim 1 and Z are alkoxy radicals having from 1 to 16 carbon atoms or aryl radicals having from 6 to 10 carbon atoms.

7. An electroluminescence material comprising one or more polymers as claimed in 1.

8. A process for producing an electroluminescence material as claimed in claim 7, which comprises a) reacting a dicarbonyl compound of the formula (II)

$$O{=}C(R^1){-}Ar^1{-}C(R^2){=}O \qquad (II)$$

with at least two equivalents of an organophosphorus compound of the formula (III)

$$Z_2\overset{O}{\underset{\|}{P}}{-}CHR^3{-}Ar^2{-}CHR^4{-}\overset{O}{\underset{\|}{P}}Z_2 \qquad (III)$$

in the presence of a base, b) polymerizing the resulting intermediate of the formula (IV)

$$Z_2\overset{O}{\underset{\|}{P}}{-}CHR^4{-}Ar^2{-}CR^3{=}CR^4{-}Ar^1{-}CR^2{=}CR^3{-}Ar^2{-}CHR^4{-}\overset{O}{\underset{\|}{P}}Z_2 \qquad (IV)$$

with a dicarbonyl compound of the formula (V)

$$O{=}C(R^5){-}Ar^3{-}C(R^6){=}O \qquad (V)$$

in the presence of a base to give a polymer comprising repeating units of the formula (I), where the symbols have the same meanings as in the formula (I) in claim 1 and Z are alkoxy radicals having from 1 to 16 carbon atoms or aryl radicals having from 6 to 10 carbon atoms and c) applying the resulting polymer comprising repeating units of the formula (I) in the form of a film to a substrate which, if desired, also comprises further layers.

9. An electroluminescence device comprising one or more active layers, wherein at least one of these active layers comprises one or more polymers as claim 1.

10. A polymer as claimed in claim 1, wherein the symbols in the formula (I) have the following meanings:

$Ar^1$, $Ar^2$, $Ar^3$ are identical or different and are

[structures: phenylene, methyl-phenylene, biphenylene]

-continued

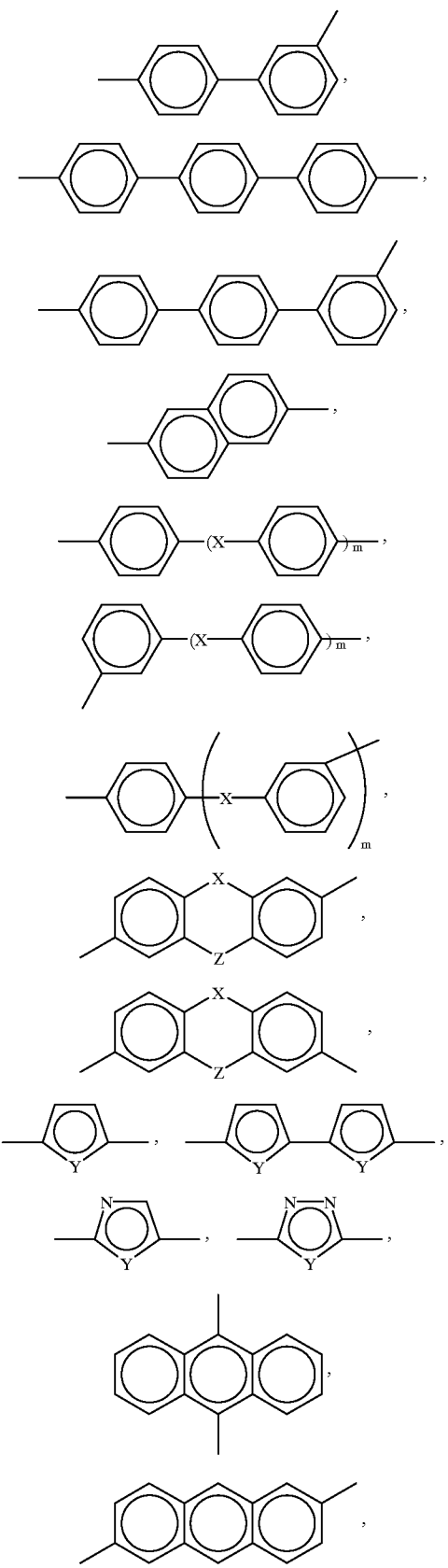

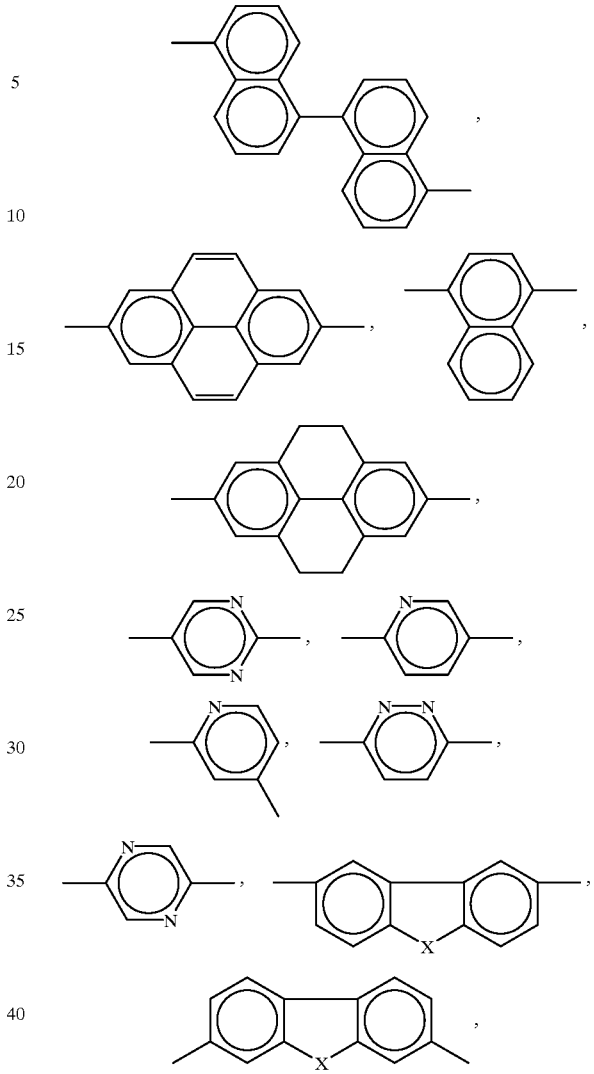

m is from 1 to 3;

Ar$^1$, Ar$^2$, Ar$^3$ may be substituted by one or more identical or different radicals R$^9$–R$^{14}$;

X, Z are identical or different and are each a single bond, —O—, —S—, —SO—, —SO$_2$—, —CO—, —CR$^9$R$^{10}$—, —CR$^{11}$=CR$^{12}$—, —CHR$^{13}$—, —CHR$^{14}$—, or —NR$^{15}$—;

Y is —O—, —S—, or —NR$^{15}$—:

R$^9$–R$^{14}$ are identical or different and are each H, an alkyl group having from 1 to 12 carbon atoms, where one or two nonadjacent CH$_2$ groups may also be replaced by —O—, —S—, —CO—, —CO—O—, —O—OC— or Si(CH$_3$)$_2$— or —CF$_3$—, —Ph, —OPh, —S—Ph, —SO—Ph, —SO$_2$—Ph, F, Cl, Br, I or —CN;

R$^{15}$ is as defined for R$^1$ and may be identical to or different from R$^1$; n 0 or 1.

11. A polymer as claimed in claim 4, wherein the symbols in the formula (I) have the following meanings:

$Ar^1$, $Ar^2$, $Ar^3$ are identical or different and are
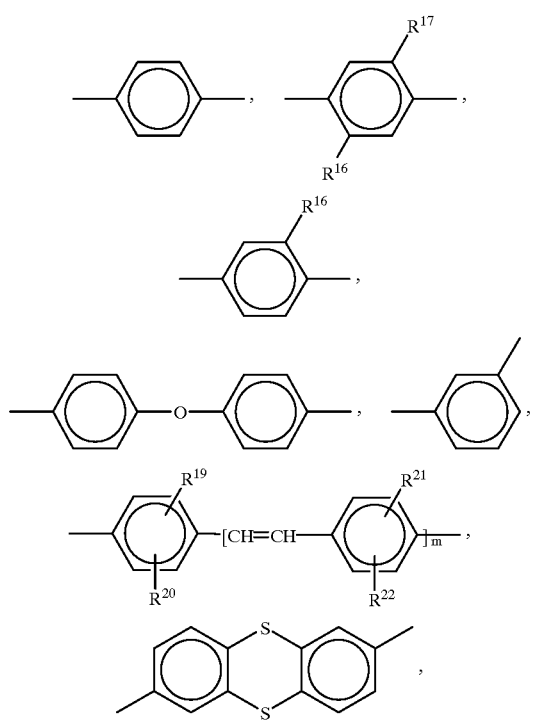
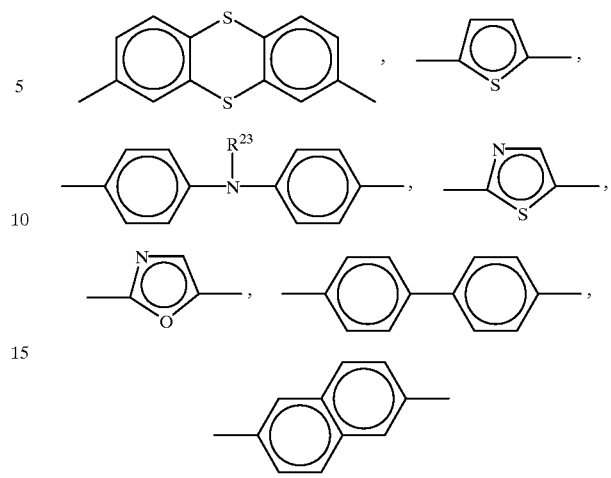
m is from 1 to 3;
$R^{16}$–$R^{23}$ are identical or different and are each F, Cl, $C_6$–$C_{10}$-aryl, a straight chain or branched alkyl or alkoxy group having from 1 to 12 carbon atoms and $R^{19-22}$ can also be H.
* * * * *